Feb. 12, 1952 T. DOMOTO Plant Pat. 1,074
CAMELLIA PLANT
Filed Oct. 19, 1950
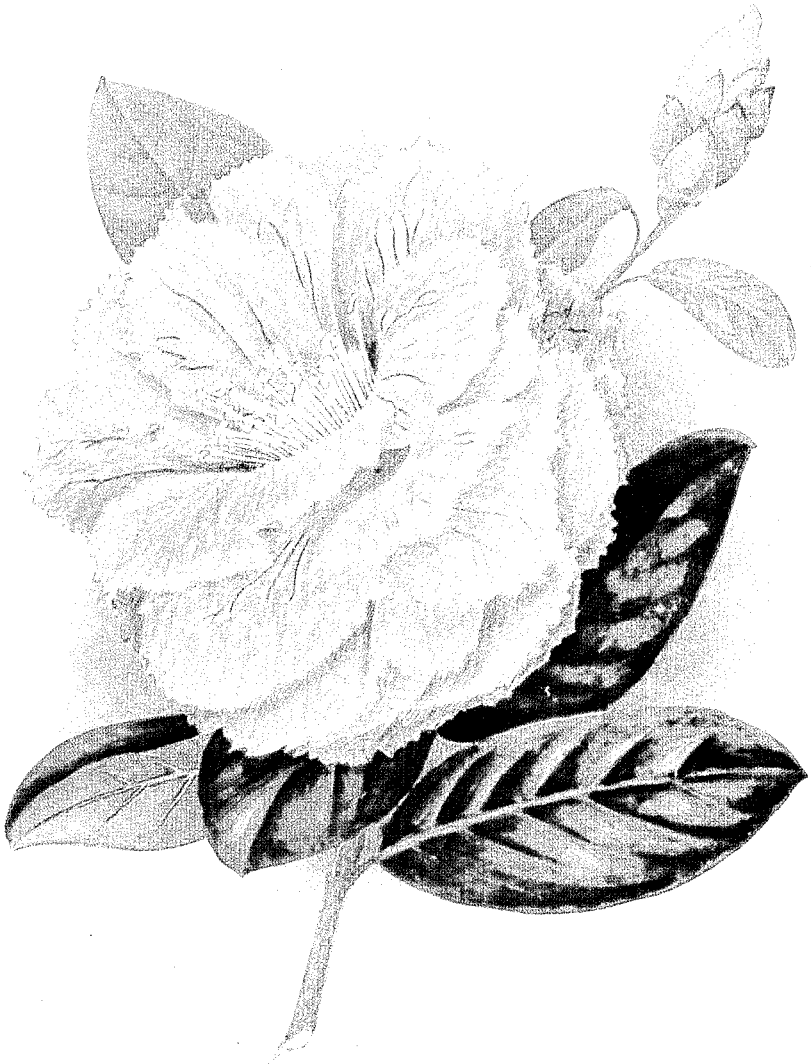
WITNESS
Addison E. Avery
INVENTOR
Toichi Domoto,
by Rummler Rummler & Shroo,
ATTYS.

Patented Feb. 12, 1952

Plant Pat. 1,074

UNITED STATES PATENT OFFICE 1,074

CAMELLIA PLANT

Toichi Domoto, Hayward, Calif.

Application October 19, 1950, Serial No. 190,957

1 Claim. (Cl. 47—60)

The present discovery relates to a new and distinct variety of Camellia japonica plant, originating as a sport of the variety known as Mathotiana Rubra (unpatented) and is the result of selection procedures carried on by me and my associates since 1943 at Hayward, Alameda County, California. The original Mathotiana Rubra plant had flowers with occasional serrated petaloids. One particular flower with the branch on which it was produced showed a few more petaloids with deeper serrations than normal for this variety. I took a scion from this particular branch and grafted the scion on to strong growing Camellia japonica understock. The resulting plant when flowers were produced on it shower more serrated petals than the original sport. The final selection was made from plants produced from such careful selection which showed serrations on practically every petal. This base plant was then used as the mother stock from which to propagate the plants herein described. The plant has been reproduced asexually by me from cuttings and its characteristics have been found to be fixed, at Hayward, California. An example of the bloom and foliage of the plant is shown in the accompanying drawing.

The distinctive feature of my new variety is the fimbriated petals of its blooms. Otherwise it has all of the characteristics of its parent.

In this California locality the flowers show an open center as in the accompanying drawing, but in areas where Mathotiana Rubra has a rosebud form, the flowers of this sport develop in that form but the serrated margin of its petals is maintained.

The petals are large, numerous, loosely overlapping and have a rose-opal color veined in a slightly darker shade of that color and the stamens and anthers are yellow. The leaves are dark green and shiny.

The following is a detailed description of this new variety.

Parentage: Sport of Mathotiana Rubra variety.
Botanic classification: Camellia japonica.
Blooming habit: Blooms profusely once in spring midseason.
Bud: Large and globular.
Flower:
- *Size.*—Very large, 4½ to 6 inches across.
- *Borne.*—Singly.
- *Shape.*—Rose-like.
- *Fragrance.*—None.
- *Petalage.*—Double, arranged irregularly and overlapped laterally.
- *Number.*—30 to 40.
- *Shape.*—Roundish with indented, recurved tips and sharply serrated fimbriate edges.
- *Color.*—Rose Opal (British Horticultural Society Chart 022, page 110).
- *Discoloration.*—None.
- *Appearance.*—Velvety.
- *Lasting quality.*—Good, both on plant and as a cut flower. Not affected by wet or hot weather and disease resistant.
- *Anthers and stamens.*—Long, yellow and conspicuously exposed to view.
- *Peduncle.*—Short.

Foliage:
- *Leaves.*—Large and glossy.
- *Color.*—Top, green (Maerz & Paul Plate 23, A, 12); bottom, green.
- *Form.*—Oblanceolate.

Plant: Bush form and vigorous growth.

I claim:

A new and distinct variety of Camellia japonica plant characterized by the fimbriated petals of its flowers, substantially as shown and described.

TOICHI DOMOTO.

No references cited.